US006790857B2

(12) United States Patent
Archer

(10) Patent No.: US 6,790,857 B2
(45) Date of Patent: Sep. 14, 2004

(54) BENZOYLECGONINE COMPOSITIONS AND METHODS FOR PRODUCING THEM

(75) Inventor: Nicholas James Archer, Mid-Lothian (GB)

(73) Assignee: Entropin, Inc., Indio, CA (US)

(*) Notice: Subject to any disclaimer, the term of this patent is extended or adjusted under 35 U.S.C. 154(b) by 0 days.

(21) Appl. No.: 10/294,858

(22) Filed: Nov. 13, 2002

(65) Prior Publication Data

US 2003/0144317 A1 Jul. 31, 2003

Related U.S. Application Data

(60) Provisional application No. 60/348,882, filed on Nov. 13, 2001.

(51) Int. Cl.[7] .................... A61K 31/46; C07D 451/02
(52) U.S. Cl. .................... 514/304; 546/131; 546/130; 546/127; 546/124; 546/112; 514/299
(58) Field of Search ................ 514/304, 299; 546/131, 130, 127, 124, 112

(56) References Cited

U.S. PATENT DOCUMENTS

| 2,893,996 A | 7/1959 | Rudner et al. ............. 260/292 |
| 2,948,730 A | 8/1960 | Rudner et al. ............. 260/292 |
| 4,469,700 A | 9/1984 | Somers ....................... 424/265 |
| 4,512,996 A | 4/1985 | Somers ....................... 514/304 |
| 4,556,663 A | 12/1985 | Somers ....................... 514/304 |
| 5,376,667 A | 12/1994 | Somers et al. ............. 514/304 |
| 5,525,613 A | 6/1996 | Wynn et al. ................ 514/304 |
| 5,559,123 A | 9/1996 | Somers et al. ............. 514/304 |
| 5,663,345 A | 9/1997 | Somers et al. ............. 546/127 |
| 5,763,456 A | 6/1998 | Wynn et al. ................ 514/304 |
| 6,077,848 A | 6/2000 | Wynn et al. ................ 514/304 |

FOREIGN PATENT DOCUMENTS

| FR | 2569563 | 3/1986 | .......... A61K/31/46 |
| WO | WO 94/15935 | 7/1994 | .......... C07D/451/12 |

OTHER PUBLICATIONS

W.H. Anderson and D.T. Stafford, "Applications of Capillary Gas Chromatography in Routine Toxicological Analyses", *J. High Resolut. Chromatogr., Chromatogr. Commun.*, 6, pp. 247–254 (1983).
E.J. Ariens and A.M. Simonis, "A Molecular basis for drug action. The interaction of one or more drugs with different receptors", *J. Pharm. Pharmacol.*, 16, pp. 289–312 (1964).
M.R. Bell and S. Archer, "L(+)–2–Tropinone", *J. Amer. Chem. Soc.*, 82, pp. 4642–4644 (1960).
R. Bingham, "Esterene in the Treatment of Rheumatoid Arthritis", *Arthritis News Today*, 2(7), pp. 1–4 (1980).
C.S. Boyer and D.R. Peterson, "Enzymatic Basis for the Transesterification of Cocaine in the Presence of Ethanol: Evidence for the Participation of Microsomal Carboxylesterases", *J. Pharmacol. Exp. Ther.*, 260(3), pp. 939–946 (1992).

M.R. Brzezinski et al., "Convenient Synthesis of Benzoylecgonine Ethyl Ester, a Homolog of Cocaine", *Synth. Commun.*, 22(7), pp. 1027–1032 (1992).
R.D. Budd, "Cocaine Radioimmunoassay—Stucture Versus Reactivity", *Clin. Toxicol.*, 18(7), pp. 773–782 (1981).
H. Bundgaard, Design of Prodrugs. Elsevier. Amsterdam, pp. 1–2 (1985).
D.T. Chia and J.A. Gere, "Rapid Drug Screening Using Toxi–Lab® Extraction Followed by Capillary Gas Chromatography/Mass Spectroscopy", *Clin. Biochem.*, 20(5), pp. 303–306 (1987).
A.J. Clark, "The Antagonism of Acetyl Choline by Atropine", *J. Physiol.*, 61, pp. 547–556 (1926).
E.J. Cone et al., "Testing Human Hair for Drug Abuse. II. Identification of Unique Cocaine Metabolites in Hair of Drug Abusers and Evaluation of Decontamination Procedures", *J. Anal. Toxicol.*, 15(5), pp. 250–255 (1991).
C. Csongar, et al., J. Prakt. Chem. 329(6) 1111–1115 (1987).
R.A. Dean et al., "Human Liver Cocaine Esterases: Ethanol–Mediated Formation of Ethylcocaine", *FASEB J.*, 5(12), pp. 2735–2739 (1991).
F. Fish and W.D.C. Wilson, "Excretion of Cocaine and its Metabolites in Man", *J. Pharm. Pharmac.*, 21 suppl., pp. 135S–138S (1969).
J.R. Fozard et al.,l "Structure–Activity Relationship of Compounds Which Block Receptors for 5–Hydroxytryptamine on the Sympathetic Nerves of the Rabbit Heart", *Br. J. Pharmacol.*, 61(3), pp. 499P–500P (1977).
J.R. Fozard et al., "Blockade of Serotonin Receptors on Autonomic Neurones by (–)–Cocaine and Some Related Compounds", *Eur. J. Pharmacol.*, 59(3–4), pp. 195–210 (1979).
J.H. Gaddum, "The Action of Adrenalin and Ergotamine on the Uterus of the Rabbit", *J. Physiol.*, 61, pp. 141–150 (1926).
J.H. Gaddum, "The Quantitative Effects of Antagonistic Drugs", *J. Physiol.*, 89, pp. 7–9 (1937).
J.M.G. Galvez and A.P. de Abram, "Cocaina: Avances en su Investigacion", *Bol. Soc. Ouim. Peru*, 56(1), pp. 12–20 (1989).

(List continued on next page.)

*Primary Examiner*—Charanjit S. Aulakh
(74) *Attorney, Agent, or Firm*—Fish & Neave; Denise L. Loring; Michele A. Kercher

(57) ABSTRACT

This invention provides a method for preparing a benzoylecgonine composition comprising the steps of:
  (a) contacting benzoylmethylecgonine and propylene glycol in the presence or absence of water to form a reaction mixture;
  (b) maintaining the reaction mixture at a temperature between about 50° and 100° C.; and
  (c) subsequently or simultaneously removing water from the reaction mixture.

This invention also provides novel benzoylecgonine and methods for producing them.

8 Claims, No Drawings

OTHER PUBLICATIONS

C. Hansch and W.J. Dunn, "Linear Relationships between Lipophilic Character and Biological Activity of Drugs", *J. Pharm. Sci.*, 61, pp. 1–19 (1972).

W.L. Hearn et al., "Cocaethylene is More Potent than Cocaine in Mediating Lethality", *Pharmacol., Biochem. Behav.*, 39(2), pp. 531–533 (1991).

W.L. Hearn et al., "Cocaethylene: A Unique Cocaine Metabolite Displays High Affinity for the Dopamine Transporter", *J. Neurochem.*, 56(2), pp. 698–701 (1991).

G.W. Hime et al., "Analysis of Cocaine and Cocaethylene in Blood and Tissues by GC–NPD and GD–Ion Trap Mass Spectrometry", *J. Anal. Toxicol.*, 15(5), pp. 241–245 (1991).

P. Jatlow et al., "Cocaethylene: A Neuropharmacologically Active Metabolite Associated with Concurrent Cocaine–Ethanol Ingestion", *Life Sci.*, 48(18), pp. 1787–1794 (1991).

J.L. Katz et al., "Comparative Behavioral Pharmacology and Toxicology of Cocaine and its Ethanol–Derived Metabolite, Cocaine Ethyl–Ester (Cocaethylene)", *Life Sci.*, 50(18), pp. 1351–1361 (1992).

A. Leo et al., "Partition Coefficients and Their Uses", *Chemical Reviews*, 71, pp. 525–616 (1971).

A.H. Lewin et al., "2β–Substituted Analogues of Cocaine. Synthesis and Inhibition of Binding to the Cocaine Receptor", *J. Med. Chem.*, 35(1), pp. 135–140 (1992).

T. Lukaszewski and W.K. Jeffery, "Impurities and Artifacts of Illicit Cocaine", *J. Forensic Sci.*, 25(3), pp. 499–507 (1980).

J. March, Advanced Organic Chemistry, McGraw Hill Book Company, New York, Second Edition, p. 363 (1977).

H.H. McCurdy, "Quantitation of Cocaine and Benzoylecgonine after JETUBE® Extraction and Derivitazation", *J. Anal. Toxicol.*, 4(2), pp. 82–85 (1980).

*Medical World News*, "FP Giving Cocaine for Arthritis is Beset But Gains a Major Ally", pp. 19–20 (1979).

A.L. Misra et al., "Physiologic Disposition and Metabolism of [$^3$H]–Ecgonine (Cocaine Metabolite) in the Rat", *Res. Commun. Chem. Pathol. Pharmacol.*, 8, pp. 55–63 (1974).

A.L. Misra and S.J. Mule, "Calcium–Binding Property of Cocaine and Some of its Active Metabolites—Formation of Molecular Complexes", *Res. Comm. Chem. Pathol. Pharmacol.*, 11(4), pp. 663–666 (1975).

A.L. Misra et al., "Disposition [$^3$H]–Benzoylnorecgonine (Cocaine Metabolite) in the Rat", *Res. Commun. Chem. Pathol. Pharmacol.*, 13(4), p. 579–584 (1976).

A.L. Misra et al., "Estimation and Disposition of [$^3$H]–Benzoylecgonine and Pharmacological Activity of Some Cocaine Metabolites", *J. Pharm. Pharmac.*, 27, pp. 784–786 (1975).

C. Moore et al., "Determination of Cocaine and its Metabolites in Brain Tissue Using High–Flow Solid–Phase Extraction Columns and High–Performance Liquid Chromatography", *Forensic Sci. Int.*, 53(2), pp. 215–219 (1992).

S.J. Mule et al., "Intracellular Disposition of [$^3$H]–Cocaine, [$^3$H]–Norcocaine, [$^3$H]–Benzoylecgonine and [$^3$H]–Benzoylnorecgonine in the Brain of Rats", *Life Sci.*, 19, pp. 1585–1596 (1976).

A. Pautard–cooper and SA. Evans, *J. Org. Chem.* 54(10) 2485–2488 (1989).

M. Perez–Reyes and A.R. Jeffcoat, "Ethanol/Cocaine Interaction: Cocaine and Cocaethylene Plasma Concentrations and Their Relationship to Subjective and Cardiovascular Effects", *Life Sci.*, 51(8), pp. 553–563 (1992).

M. Polášek et al., "Determination of Limiting Ionic Mobilities and Dissociation Constants of Some Local Anaesthetics", *J. Chromatogr.*, 596, pp. 265–270 (1992).

RH Prager and Z. Yurui, *Aust. J. Chem.* 42(6) 1003–1005 (1989).

F.K. Rafla and R.L. Epstein, "Identification of Cocaine and its Metabolites in Human Urine in the Presence of Ethyl Alcohol", *J. Anal. Toxicol.*, 3(2), pp. 59–63 (1979).

M.E.A. Reith et al., "Locomotor Effects of Cocaine, Cocaine Congeners and Local Anesthetics in Mice", *Pharmacol. Biochem. Behav.*, 23(5), pp. 831–836 (1985).

M.E.A. Reith et al., "Structural Requirements for Cocaine Congeners to Interact with [$^3$H] Batrachotoxinin a 20–α–Benzoate Binding Sites on Sodium Channels in Mouse Brain Synaptosomes", *J. Biol. Chem.*, 261(16), pp. 7300–7305 (1986).

M.E.A. Reith et al., "Structural Requirements for Cocaine Congeners to Interact with Dopamine and Serotonin Uptake Sites in Mouse Brain and to Induce Stereotyped Behavior", *Biochem. Pharmacol.*, 35(7), pp. 1123–1129 (1986).

S.M. Roberts et al., "Cocaethylene Hepatoxicity in Mice", *Biochem. Pharmacol.*, 43(9), pp. 1989–1995 (1992).

S.M. Roberts et al., "An Assay for Cocaethylene and Other Cocaine Metabolites in Liver Using High–Performance Liquid Chromatography", *Anal. Biochem.*, 202(2), pp. 256–261 (1992).

R.H. Rohrbaugh and P.C. Jurs, "Prediction of Gas Chromatographic Retention Indexes for Diverse Drug Dompounds", *Anal. Chem.*, 60(20), pp. 2249–2253 (1988).

H.–L. Schmidt and G. Werner, "Synthetischer Einbau von $^{14}$C in (–)–Cocain,(–)–Ekgonin und Derivate", *Ann.*, pp. 184–194 (1962).

R.M. Smith, "Ethyl Esters of Arylhydroxy– and Arylhydroxymethoxycocaines in the Urines of Simultaneous Cocaine and Ethanol Users", *J. Anal. Toxicol.*, 8(1), pp. 38–42 (1984).

R.P. Stephenson, "A Modification of Receptor Theory", *Brit. J. Pharmacol.*, 11, pp. 379–393 (1956).

D.L. Von Minden and N.A. D'Amato, "Simultaneous Determination of Cocaine and Benzoylecgonine in Urine by Gas–liquid Chromatography", *Anal. Chem.*, 49(13), pp. 1974–1977 (1977).

G. Werner and K.H. Störr, "Labelled Tropane Alkaloids. VI. Synthesis of [N–methyl–T1] Psicain–nue and of Polytopically Tritiated Psicain", *Liebios Ann. Chem.*, pp. 1650–1654 (1974).

J.J. Woodward et al., "Cocaethylene Inhibits Dopamine Uptake and Produces Cocaine–Like Actions in Drug Discrimination Studies", *Eur. J. Pharmacol.*, 197(2–3), pp. 235–236 (1991).

I. Zimányi et al., "Effect of Cocaine and Cocaine Congeners on Veratridine–Induced Depolarization in Mouse Cerebrocortical Synaptoneurosomes", *J. Neurosci. Res.*, 22(2), pp. 201–208 (1989).

BENZOYLECGONINE COMPOSITIONS AND METHODS FOR PRODUCING THEM

CROSS-REFERENCE TO RELATED APPLICATIONS

This application claims the benefit under 35 U.S.C. §119(e) of U.S. Provisional Application No. 60/348,882, filed Nov. 13, 2001.

TECHNICAL FIELD

This invention relates to novel compositions comprising benzoylecgonine and structurally related compounds, and methods for producing them.

BACKGROUND

Compositions comprising benzoylecgonine and structurally-related chemical compounds (such as ecgonine, ecgonidine and derivative thereof) are useful in preventing and treating a number of important diseases and disorders (see, for example, U.S. Pat. Nos. 4,469,700; 4,512,996; 4,556,663; 5,376,667; 5,559,123 and 5,663,345; each of which is hereby incorporated herein in its entirety). Particularly useful benzoylecgonine-related compounds include the 2-hydroxypropyl ester derivatives of benzoylecgonine, ecgonine, and ecgonidine. Methods for producing compositions comprising these 2-hydroxypropyl esters have been described in U.S. Pat. No. 5,376,667. The preferred method described in U.S. Pat. No. 5,376,667 utilizes the step of heating cocaine base in a propylene glycol/water solution (95% propylene glycol/5% water w/w) at 50° C. for 12 days, after which time less than 0.1% of the cocaine base starting material remained (see column 7, lines 3–17). The composition produced by this method comprises approximately 5% w/w of an active component mixture in propylene glycol, wherein the active component mixture comprises approximately 65% benzoylecgonine, 2% ecgonidine and 5% and 6%, respectively, of the 2-hydroxypropyl derivatives of benzoylecgonine and ecgonidine. It has recently been discovered by the inventors hereof that removal of water during the reaction used to produce the 2-hydroxypropyl derivatives of benzoylecgonine and ecgonidine helps drive the reaction to the desired products and, furthermore, removal of water during or subsequent to the reaction results in a composition with enhanced stability. The novel method for the production of the compositions comprising 2-hydroxypropyl derivatives of benzoylecgonine and ecgonidine and the enhanced stability of the resulting composition may provide advantages over the prior art methods and compositions that can be appreciated by one of skill in the art.

SUMMARY

The invention described herein fulfills the needs described above. In one embodiment, this invention provides a method for preparing a benzoylecgonine composition comprising the steps of:

(a) contacting benzoylmethylecgonine and propylene glycol in the presence or absence of water to form a reaction mixture;

(b) maintaining the reaction mixture at a temperature between about 50° and 100° C; and (c) subsequently or simultaneously removing water from the reaction mixture.

In another embodiment, this invention provides novel benzoylecgonine compositions comprising at least about 2% 2-hydroxypropyl benzoylecgonine esters, at least about 2% 2-hydroxypropyl ecgonidine esters, less than about 0.1% benzoylmethylecgonine and between about 0% and about 4% water.

The details of one or more embodiments of the invention are set forth in the accompanying drawings and the description below. Other features, objects, and advantages of the invention will be apparent from the description and drawings, and from the claims.

DETAILED DESCRIPTION

As used herein:

Percentage content of particular components of a composition refers to the percentage of the weight of that component represented in the weight of the final composition. For example, a composition comprising 5% water is 5% water w/w of the composition.

The term "benzoylmethylecgonine" or "BME" refers to the chemical entity 3-benzoyloxy-2-carbomethyoxy-8-methyl-8-azabicyclo[3.2.1]octane. BME can exist in four diastereomeric forms (cocaine, pseudococaine, allococaine and allopseudococaine) and each diastereomer has two optical antipodes. Any one of these compounds or any combination of more than one of these compounds is encompassed by the invention herein. BME is typically prepared as a salt (e.g., cocaine HCl) or a reduced base (e.g., cocaine alkaloid) according to known methods.

The terms "2-hydroxypropyl ester", "2-hydroxypropyl ester derivatives", "2-HP derivatives" and other similar terms used herein, refer to the 2-hydroxypropyl ester derivatives of benzoylecgonine, ecgonine and/or ecgonidine. When these terms are used in general herein, they are meant to refer to any one or more of these 2-hydroxypropyl ester derivatives.

The term "substantially all", when referring to the reaction of benzoylmethylecgonine, means that more than approximately 95% of the benzoylmethylecgonine has reacted, preferably more than approximately 99%, more preferably, more than approximately 99.5% and most preferably, more than approximately 99.9%.

This invention provides a method for preparing a benzoylecgonine composition comprising the steps of:

(a) contacting benzoylmethyleegonine and propylene glycol in the presence or absence of water to form a reaction mixture;

(b) maintaining the reaction mixture at a temperature between about 50° and 100° C.; and (c) subsequently or simultaneously removing water from the reaction mixture.

The methods of this invention advantageously produce a benzoylecgonine composition that is proportionately higher in 2-hydroxypropyl ester derivatives and/or demonstrates enhanced stability as compared to benzoylecgonine compositions comprising or produced in excess water. Using the methods of this invention, it is possible to enhance the relative content of one or more specific 2-HP ester derivatives. In particular, the methods of this invention may be used to produce a benzoylecgonine composition that has an enhanced relative content of the 2-hydroxypropyl esters of benzoylecgonine (2-HP BEc). It is believed that 2-HP BEc may have superior activity for particular indications (including, without limitation, one or more of the indications described in U.S. Pat. Nos. 4,469,700; 4,512,996; 4,556,663; 5,376,667; 5,559,123 and 5,663,345) as compared with other 2-HP esters.

The methods of this invention may be carried out in any suitable reaction vessel, including glass and stainless steel flasks. The starting material, benzoylmethylecgonine, may be used as the free base prepared by alkaline reduction of cocaine HCl (converted using known techniques such as, for example, U.S. Pat. No. 5,376,667, column 11, lines 45–52) or directly from the trophane alkaloid (which is a preferred starting material). These materials can be obtained commercially or may be prepared using known synthetic processes. Although the reaction may be quenched at any time, the reaction is preferably maintained until substantially all of the benzoylmethylecgonine has reacted. In one preferred embodiment, the reaction is monitored by observing the amount of 2-HP BEc produced in addition to observing the disappearance of benzoylmethylecgonine. Ideally, the reaction should be quenched when the maximum amount of 2-HP BEc has been produced. The amount of benzoylmethylecgonine or of 2-HP BEc can be monitored during the course of the reaction using known techniques, such as gas chromatography, high performance liquid chromatography (HPLC) and/or mass spectrophotometry. These and other like techniques are well known to those of ordinary skill in the art and have been described in U.S. Pat. No. 5,376,667 and elsewhere.

Preferably, in step (a), water is present at a ratio of water to propylene glycol of approximately 1:19. Accordingly, in one preferred embodiment, water represents approximately 5% w/w of the reaction mixture, the propylene glycol represents the remaining 95% (w/w).

In a preferred embodiment, water is added to the propylene glycol prior to addition of benzoylmethylecgonine and prior to or during heating. Preferably, the propylene glycol/water solution is stirred during heating. The reaction mixture is preferably heated to between about 45° and 80° C., more preferably, to between about 50° and 70° C. and most preferably, to approximately 60° C. prior to adding the benzoylmethylecgonine. At approximately 60° C., the reaction time is approximately twice as fast as that exemplified in Example 3 of U.S. Pat. No. 5,376,667. It is anticipated that heating of the reaction mixture above about 60° C. will similarly result in a decreased reaction time. However, the product made at temperatures significantly above about 60° may develop an undesirable color unless the pressure is reduced accordingly. Therefore, it is possible to run the reaction of this invention under reduced pressure and higher temperatures to produce a final product in the shortest time that has the most desirable appearance and profile.

It should be noted that the reaction may be carried out successfully in either the presence or the absence of water. In fact, the yield of 2-hydroxypropyl esters of benzoylecgonine may be enhanced by excluding water from the reaction mixture. Regardless of whether or not water is initially added to the reaction mixture, we have found that the removal of water during or subsequent to the reaction helps to drive the reaction to the desired 2-hydroxypropyl ester derivatives and furthermore, results in a more stable final product. Water is preferably removed from the reaction mixture during the course of the reaction. Water may be removed by any known means, such as by use of water scavengers (such as molecular sieves), vacuum distillation, by fitting the reaction vessel with an open reflux condenser or conducting the reaction under a flow of an inert gas, such as nitrogen or argon (preferably, dry nitrogen or argon) (or any combination of such means). Preferably, the method of this invention is conducted in a vessel fit with an open reflux condenser, in which a stream of dry nitrogen is blown over the surface of the reaction mixture. The inventors have found that by conducting the reaction under these preferred conditions, significantly less water is present in the final product as compared to prior methods (e.g., typically approximately 1%–2% versus approximately 5%). In addition, it was also found that these reaction conditions result in a final product composition that is higher in overall content of 2-hydroxypropyl ester derivatives than if the water is not removed during the reaction (at least about 2% benzoylecgonine and 2-hydroxypropyl esters of ecgonidine, respectively). Although removal of water during the course of the reaction is preferred, water can be removed after the reaction is complete, or water may be removed both during and after the reaction is complete, if desired. Molecular sieves or other conventional drying agents (such as, for example, magnesium sulfate trihydrate) may be used for this purpose.

It has been discovered surprisingly that the removal of water during the reaction and/or from the final product leads to increased stability of the resultant composition. It has also been surprisingly determined that performing the reaction in the absence of water results in an improved conversion of starting material to desired product. Without wishing to be bound by theory, we believe that these surprising results are a consequence of the particular biochemical pathways leading from the benzoylmethyleegonine to the production of the hydroxypropyl esters. Particular features of this pathway are illustrated below:

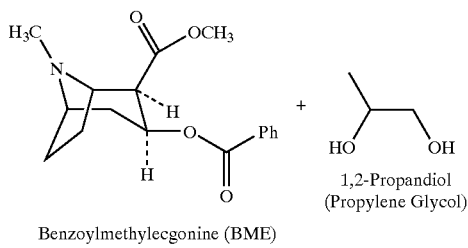

-continued

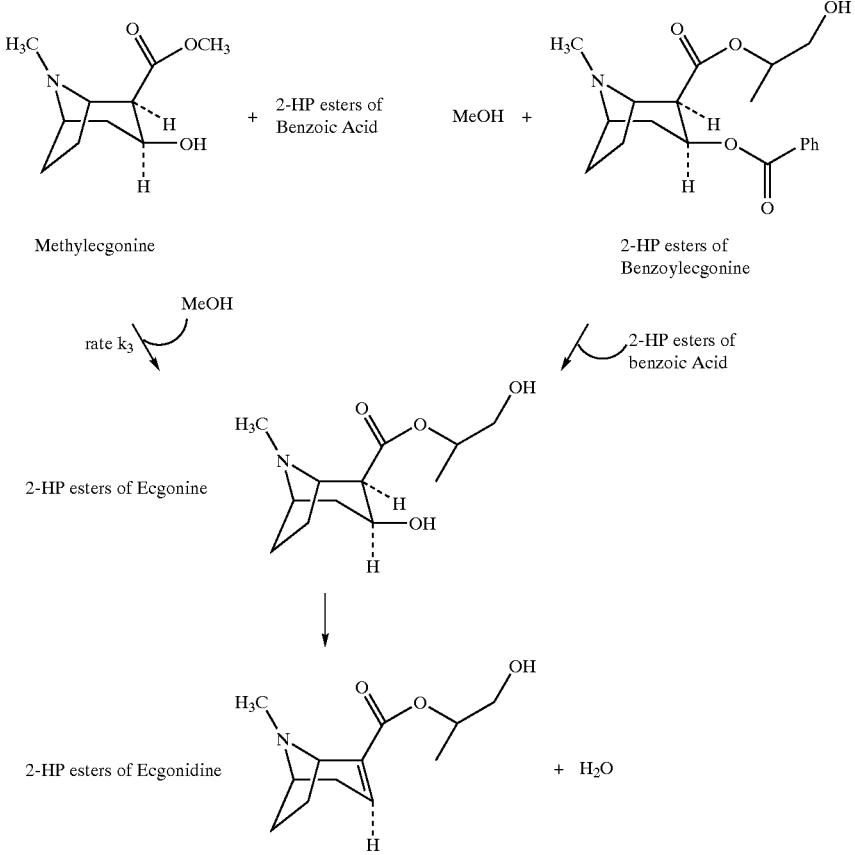

Methylecgonine

2-HP esters of Benzoylecgonine

2-HP esters of Ecgonine

2-HP esters of Ecgonidine

It should be noted that transesterification rates $k_1$, $k_2$, and $k_3$ are impacted by the presence or absence of water, the temperature and pressure of the reaction. In addition, it should be noted that the reaction of benzoylmethylecgonine results in the production of water.

As detailed above, the methods of this invention are useful for producing improved benzoylecgonine compositions. Without limiting the generality of the foregoing, the compositions produced by the methods of this invention possess one or more of the following properties: enhanced stability (e.g., having a longer shelf life), enhanced content of 2-hydroxypropyl ester derivatives, and more cost effective manufacturing. Preferred compositions of this invention are benzoylecgonine compositions comprising at least about 2% 2-hydroxypropyl benzoylecgonine esters, at least about 2% 2-hydroxypropyl ecgonidine esters, less than about 0.1% benzoylmethylecgonine esters and less than about 4% water.

Without wishing to be bound by theory, we believe that the enhanced stability seen in the compositions of the instant invention results from the removal of water from the compositions. It is believed that over time, water may facilitate ester hydrolysis of the benzoylecgonine compositions. By removing water, this process is restricted. In addition, we have found surprisingly that the reaction that converts benzoylmethyleegonine to the 2-hydroxypropyl esters proceeds via transesterification, rather than hydrolysis followed by esterification. Thus, removal of water drives the reaction to form greater amounts of 2-hydroxypropyl ester derivatives and produces a final product more concentrated (enriched) in 2-hydroxypropyl ester derivatives, versus the underivatized benzoylecgonine, ecgonine and ecgonidine compounds. Lipophilic compounds, such as the 2-hydroxypropyl derivatives, are likely to possess enhanced pharmacological activity as compared to the more hydrophilic parent compounds. For example, the 2-hydroxypropyl derivatives will be more readily absorbed through the skin when administered topically, being more easily transported through the lipophilic sebum environment of the hair follicles (Int. J. Pharm. 220:63–75, 2001).

EXAMPLES

The following specific examples are to be construed as merely illustrative, and not limitative of the remainder of the disclosure in any way.

Cocaine alkaloid was prepared by basification of cocaine HCl in an aqueous 10% potassium hydroxide solution until pH>10. The solution was then filtered and the slurry washed with water. The cocaine base was dried in an oven at 60° C. for at least 18 hours before being used as input to the following reactions.

| | Percent w/w | | | |
|---|---|---|---|---|
| Component | Example 1 | Example 2 | Example 3 | Example 4 |
| Water | 1.0 | 0.40 | 0.1 | 4.96 |
| Bec | 4.9 | 4.0 | 0.4 | 6.3 |
| BA | 0.88 | 1.0 | 2.2 | 0.4 |
| 2-HP BEc | 1.43 | 1.5 | 2.4 | 0.76 |
| 2-HP Ecd | 1.35 | 1.6 | 4.7 | 0.8 |
| 2-HP BA | 1.03 | 1.15 | 2.2 | 0.4 |

-continued

| Component | Percent w/w | | | |
|---|---|---|---|---|
| | Example 1 | Example 2 | Example 3 | Example 4 |
| Methyl Ecd | 0.37 | 0.4 | 0.45 | 0.4 |
| Ecd | 0.02 | 0.02 | 0.02 | ND |

BEc = benzoylecgonine;
Ec = ecgonine;
BA = benzoic acid;
Ecd = ecgonidine

Example 1

Inert Gas Flow 2.0 g of cocaine alkaloid was added to a 50 ml glass stoppered jacketed flask, followed by 17 g of propylene glycol and 1.0 g of water. The contents were stirred and placed under a steady stream of dry nitrogen with an open water condenser, the solution was maintained at 50° C. until the unreacted cocaine was less than 0.1% w/w.

Example 2

Vacuum 2.0 g of cocaine alkaloid was added to a 50 ml glass stoppered jacketed flask, followed by 17 g of propylene glycol and 1.0 g of water. The contents were stirred and placed under a vacuum (25 mm/Hg), and the solution was maintained at 50° C. until the unreacted cocaine was less than 0.1% w/w.

Example 3

Absence of Water 2.0 g of cocaine alkaloid was added to a 50 ml glass stoppered jacketed flask, followed by 18 g of propylene glycol. The contents were stirred and placed under a nitrogen atmosphere, the solution was maintained at 55° C. until the unreacted cocaine was less than 0.1% w/w.

Example 4

5% w/w Water 2.0 g of cocaine alkaloid was added to a 50 ml glass stoppered jacketed flask, followed by 17 g of propylene glycol and 1.0 g of water. The contents were stirred and placed under a nitrogen atmosphere, the solution was maintained at 50° C. until the unreacted cocaine was less than 0.1% w/w.

Example 5

Stability Testing (Absence of Water)

The following table shows the changes in the relative amounts of particular components for the composition produced in Example 3 at 60° C. The last two columns represent the stability of the composition at 25° C. and 40° C. after 13 days.

| Temperature → | Reaction time at 60° C. | | | | | STABILITY | |
|---|---|---|---|---|---|---|---|
| | | | | | | 25° C. | 40° C. |
| Days → | 6 | 8 | 11 | 13 | 15 | 13 days | 13 days |
| Ecd | | | | | | | |
| BA | 12.59 | 16.06 | 21.22 | 24.05 | 26.05 | 27.35 | 28.75 |
| Methyl Ecd | 1.63 | 1.63 | 1.51 | 1.47 | 1.42 | 1.33 | 1.26 |
| 2-HPE Ecd (A + B) | 3.39 | 4.79 | 7.05 | 8.29 | 9.31 | 9.26 | 9.85 |
| 2-HPE Ecd (C) | 0.64 | 0.91 | 1.31 | 1.54 | 1.75 | 1.78 | 1.89 |
| BEe | 2.16 | 2.58 | 3.52 | 3.79 | 4.097 | 3.99 | 4.28 |
| 2-HPE BEc (A) | 11.17 | 11.00 | 10.11 | 9.03 | 7.92 | 7.72 | 6.82 |
| 2-HPE BEc (B) | 17.12 | 16.14 | 13.57 | 11.78 | 10.42 | 9.79 | 8.72 |
| 2-HPE BEc (C) | 19.70 | 17.75 | 14.31 | 12.15 | 10.42 | 8.97 | 7.81 |
| BME | 8.98 | 4.91 | 2.81 | 2.14 | 1.76 | 1.19 | 0.90 |
| 2-HPE BA (A) | 7.11 | 8.83 | 11.58 | 12.93 | 14.04 | 15.35 | 16.30 |
| 2-HPE BA (B) | 4.59 | 5.47 | 6.14 | 6.93 | 7.58 | 7.92 | 8.50 |
| BME % (w/w) | 0.75 | 0.40 | 0.21 | 0.16 | 0.13 | 0.08 | 0.06 |
| $H_2O$ content (w/w) | 0.11 | 0.10 | 0.46 | 0.12 | 0.12 | ND | ND |

BEc = benzoylecgonine;
Ec = ecgonine;
BA = benzoic acid;
Ecd = ecgonidine;
2-HPE = 2 hydroxypropyl ester;
designations A, B and C indicate different isomers of the named compound;
BME = benzoylmethylecgonine.

Example 6

Stability Testing (Initial 5% w/w water)

The following table shows the changes in the relative amounts of particular components for the composition produced in Example 4 at 50° C. The last two columns represent the stability of the composition at 25° C. and 40° C. after 13 days.

| Temperature → | Reaction time at 50° C. | | | | | STABILITY | |
|---|---|---|---|---|---|---|---|
| | | | | | | 25° C. | 40° C. |
| Days → | 6 | 8 | 12 | 14 | 16 | 13 days | 13 days |
| Ecd | | | | | | | |
| BA | 5.64 | 6.64 | 8.13 | 8.46 | 8.99 | 9.17 | 9.68 |
| Methyl Ecd | 0.48 | 0.70 | 0.85 | 1.05 | 1.00 | 0.86 | 0.80 |
| 2-HPE Ecd (A + B) | 1.00 | 1.79 | 2.25 | 2.28 | 2.43 | 2.38 | 2.61 |
| 2-HPE Ecd (C) | 0.73 | 0.27 | 0.42 | 0.43 | 0.47 | 0.48 | 0.53 |
| BEc | 41.61 | 48.83 | 59.3 | 62.2 | 63.8 | 64.02 | 66.31 |
| 2-HPE BEc (A) | 4.67 | 4.54 | 3.71 | 3.22 | 2.79 | 2.49 | 1.82 |
| 2-HPE BEc (B) | 7.42 | 6.66 | 4.71 | 3.92 | 3.30 | 2.93 | 2.09 |
| 2-HPE BEc (C) | 10.66 | 9.41 | 5.40 | 4.38 | 3.62 | 3.30 | 2.18 |
| BME | 14.48 | 8.11 | 2.31 | 1.44 | 0.95 | 0.84 | 0.46 |
| 2-HPE BA (A) | 4.61 | 5.12 | 6.92 | 6.98 | 7.20 | 7.48 | 7.74 |
| 2-HPE BA (B) | 2.55 | 2.88 | 3.16 | 3.32 | 3.53 | 3.72 | 4.01 |

-continued

| | Reaction time at 50° C. | | | | | STABILITY | |
| --- | --- | --- | --- | --- | --- | --- | --- |
| Temperature → | | | | | | 25° C. | 40° C. |
| Days → | 6 | 8 | 12 | 14 | 16 | 13 days | 13 days |
| BME % (w/w) | 1.25 | 0.75 | 0.19 | 0.11 | 0.08 | 0.07 | 0.04 |
| H$_2$O content (w/w) | 4.85 | 4.81 | 4.15 | 4.81 | 4.76 | ND | ND |

BEc = benzoylecgonine;
Ec = ecgonine;
BA = benzoic acid;
Ecd = ecgonidine;
2-HPE = 2 hydroxypropyl ester;
designations A, B and C indicate different isomers of the named compound;
BME = benzoylmethylecgonine.

Conclusion: The examples shown above demonstrate that the methods according to this invention produce a benzoylecgonine composition having enhanced content of 2-hydroxypropyl derivatives and an improved stability profile. In Example 5, the total amount of hydroxypropyl benzoylecgonine esters (2-HPE Bec(A), 2-HPE Bec(B) and 2-HPE Bec(C) at the end of the reaction (and at the start of the stability trial) represents 28.8% of the composition and after 13 days at 40° C., 81% of the hydroxypropyl benzoylecgonine esters remain. In Example 6, the total amount of hydroxypropyl benzoylecgonine esters at the end of the reaction (and at the start of the stability trial) represents 9.71% of the composition and after 13 days at 40° C., only 61% of the hydroxypropyl benzoylecgonine esters remain.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. A method for preparing a benzoylecgonine composition comprising the steps of:

(a) contacting benzoylmethylecgomne and propylene glycol in the presence or absence of water to farm a reaction mixture;

(b) maintaining the reaction mixture at a temperature between about 50° and 100° C. until substantially all of the benzoylmethylecgonine has reacted; and (c) removing water from the reaction mixture, wherein said water is removed: (i) during the course of the reaction; or (ii) both during the course of the reaction and after the reaction is complete.

2. The method according to claim 1, wherein step (a) is performed in the absence of water.

3. The method according to claim 1, wherein the water is present in step (a) in an amount equal to approximately 0–5% by weight of the reaction mixture.

4. The method according to claim 1, wherein the temperature of step (b) is approximately 60° C.

5. The method according to claim 1, wherein water is removed from the reaction mixture in step (c) by using an open reflux condenser.

6. The method according to claim 1 or 4, wherein the reaction is conducted under a stream of inert gas.

7. The method according to claim 6, wherein the inert gas is dry nitrogen.

8. The method according to claim 6, wherein the inert gas is dry argon.

* * * * *

UNITED STATES PATENT AND TRADEMARK OFFICE
CERTIFICATE OF CORRECTION

PATENT NO.    : 6,790,857 B2
DATED         : September 14, 2004
INVENTOR(S)   : Nicholas J. Archer It is certified that error appears in the above-identified patent and that said Letters Patent is hereby corrected as shown below:

Column 10,
Line 6, change "benzoylmethylecgomne" to -- benzoylmethylecgonine --.
Line 7, change "farm" to -- form --.

Signed and Sealed this

Sixteenth Day of August, 2005

JON W. DUDAS
*Director of the United States Patent and Trademark Office*